US009045781B2

(12) United States Patent
Marshall et al.

(10) Patent No.: US 9,045,781 B2
(45) Date of Patent: *Jun. 2, 2015

(54) PROCESS FOR THE PRODUCTION OF OPTICALLY-ACTIVE ESTERS OF LACTIC ACID AND LACTYLLACTIC ACID

(75) Inventors: Edward Leslie Marshall, Greater London (GB); Jade Jocelyn Afriye Osei-Tutu, Greater London (GB); Stephen Alexander Calder Smith, Greater London (GB)

(73) Assignee: Plaxica Limited (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/232,296

(22) PCT Filed: Jul. 16, 2012

(86) PCT No.: PCT/GB2012/051695
§ 371 (c)(1),
(2), (4) Date: Jan. 13, 2014

(87) PCT Pub. No.: WO2013/011295
PCT Pub. Date: Jan. 24, 2013

(65) Prior Publication Data
US 2014/0141475 A1 May 22, 2014

(30) Foreign Application Priority Data

Jul. 15, 2011 (GB) .................................. 1112296.7
Jul. 15, 2011 (GB) .................................. 1112297.5
Jun. 11, 2012 (GB) .................................. 1210275.2

(51) Int. Cl.
C12P 33/04 (2006.01)
C12P 7/62 (2006.01)
C12P 41/00 (2006.01)
C12P 7/56 (2006.01)
C12P 17/06 (2006.01)

(52) U.S. Cl.
CPC ................. *C12P 7/62* (2013.01); *C12P 41/003* (2013.01); *C12P 7/56* (2013.01); *C12P 17/06* (2013.01)

(58) Field of Classification Search
USPC ................................................. 435/139, 135
See application file for complete search history.

(56) References Cited

U.S. PATENT DOCUMENTS 2,371,281 A 3/1945 Claborn
4,835,293 A * 5/1989 Bhatia ........................... 549/274
5,274,127 A * 12/1993 Sinclair et al. ................ 549/274
6,277,951 B1 8/2001 Gruber et al.
7,829,740 B2 11/2010 Enomoto et al.

FOREIGN PATENT DOCUMENTS

| CA | 2734102 A1 | 3/2010 |
|---|---|---|
| EP | 0657447 A1 | 6/1995 |
| GB | 2484674 A | 4/2012 |
| JP | 2009195149 A | 9/2009 |
| KR | 20050103691 A | 11/2005 |
| KR | 10-0592794 B1 | 6/2006 |
| WO | 2004/081220 A2 | 9/2004 |
| WO | 2010/005235 A2 | 1/2010 |
| WO | 2010/105142 A1 | 9/2010 |

OTHER PUBLICATIONS

Emel'yanenko et al, "The Thermodynamic Properties of S-Lactic Acid", Russian Journal of Physical Chemistry A, 2919, 84, No. 9, p. 1491-1497.
Findrik et al, "Evaluation of factors influencing the enantioselective enzymatic esterification of lactic acid in ionic liquid" Bioprocess Biosyst Eng., 2012, 35, p625-635.
Groot and Boren, "Life cycle assessment of the manufacture of lactide and PLA biopolymers from sugarcane in Thailand", Int J Life Cycle Assess, 2010, 15, p. 970-984.
Idris and Bukhari, "Immobilized *Candida antarctica* lipase B: Hydration, stripping off and application in ring opening polyester synthesis", Biotechnology Advances, 2012, 30, p. 550-556.
Jeon et al, "Synthesis of alkyl (R)-lactates and alkyl (S,S)-O-lactyl-lactates by alcoholysis of rac-lactide using Novozym 435" Tetrahedron Letters, 2006, 47, p. 6517-6520.
Jeon et al, "Lipase-catalysed enantioselective synthesis of R-lactide from alkyl lactate to produce PDLA (poly D-lactic acid) and stereocomplex PLA (poly lactic acid)", American Chemical Society, 241st ACS National Meeting, Mar. 27-31 2011, p. 260-261 (Abstract).
Jeon et al, "Improved catalysis of Candida antarctica lipase B (CALB) through protein engineering for conversion of Rlactide from alkyl R-lactate in organic solvent", The Korean Society for Biotechnology and Bioengineering, 2011 Spring Meeting, Apr. 14-16 2011, p. 22.
Kazlauskas et al, "A Rule to Predict Which Enantiomer of a Secondary Alcohol Reacts Faster in Reactions Catalyzed by Cholesterol Esterase, Lipase from *Pseudomonas cepacia,* and Lipase from *Candida rugosa*", J. Org. Chem., 1991. 56, p. 2656-2665.
Lee et al, "Highly Enantioseslective Acylation of rac-Alkyl Lactates Using *Candida antarctica* Lipase B", Organic Process Research and Development, 2004, 8, p948-951.
Lunt, "Large-scale production, properties and commercial applications of polylactic acid polymers", Polymer Degradation and Stability, 1998, 59, p. 145-152.

(Continued)

*Primary Examiner* — Ralph Gitomer
(74) *Attorney, Agent, or Firm* — Kramer Levin Naftalis & Frankel LLP

(57) ABSTRACT

A process for treating a mixture of R,R- and S,S-lactide is provided. The process involves contacting the mixture with an aliphatic alcohol and an enzyme in the presence of a ketone solvent to produce a mixture comprising aliphatic ester of lactic acid corresponding to one lactide enantiomer, and the aliphatic ester of lactyllactic acid corresponding to the other lactide enantiomer. Also provided are processes for the production of S-lactic acid, S,S-lactide, poly-S-lactic acid, R-lactic acid, R,R-lactide, poly-R-lactic acid and stereocomplex polylactic acid.

20 Claims, No Drawings

(56) References Cited

OTHER PUBLICATIONS

Matsumoto et al, "Enzymatic and whole-cell synthesis of lactate-containing polyesters: toward the complete biological polyesters: toward the complete biological production of polylactate", Appl. Microbiol. Biotechnol., 2010, 85, p. 921-932.

Nemeth et al, "Asymmetric Lactic Acid Esterification with Biocatalysts in Ionic Liquid", Hungarian Journal of Industrial Chemistry, 2011, 39, p. 419-425.

Numata et al, "Branched Poly(lactide) Synthesized by Enzymatic Polymerization: Effects of Molecular Branches and Stereochemistry on Enzymatic Degradation and Alkaline Hydrolysis", Biomacromolecules, 2007, 8, p. 3115-3125.

Ohara et al, "Optical resolution of n-butyl D- and L-lactates using immobilized lipase catalyst", Journal of Bioscience and Bioengineering, 2011, 111, p. 19-21.

Shuklov et al, "Studies on the epimerization of diastereomeric lactides", Tetrahedron Letters, 2011, 52, p. 1027-1030.

Smith and Claborn, "Lactic Esters Preparation and Properties", Industrial and Engineering Chemistry, 1940, 32, No. 5, p. 692-694.

Takwa et al, "Rational redesign of *Candida antarctica* lipase B for the ring opening polymerization of D,D-lactide", Chem. Commun., 2011, 47, p. 7392-7394.

Takwa, Lipase Specificity and Selectivity, Doctoral Thesis, Royal Institute of Technology, School of Biotechnology, Department of Biochemistry, Stockholm, Sweden, 2010.

Tsukegi et al, "Racemization behavior of L,L-lactide during heating", Polymer Degradation and Stability, 2007, 92, p. 552-559.

Yang and Liu, "Improved preparation of D, L-lactide from D, L-lactic acid using microwave irradiation", Polymer Bulletin, 2008, 61, p. 177-188.

\* cited by examiner

PROCESS FOR THE PRODUCTION OF OPTICALLY-ACTIVE ESTERS OF LACTIC ACID AND LACTYLLACTIC ACID

This application is the United States national phase filing of the corresponding international application number PCT/GB2012/051695, filed on Jul. 16, 2012, which claims priority to and benefit of GB Application No. 1112297.5, filed Jul. 15, 2011; GB Application No. 1112296.7, filed Jul. 15, 2011; and GB Application No. 1210275.2, filed Jun. 11, 2012 which applications are hereby incorporated by reference in their entirety.

The present invention relates to the production of single enantiomers of lactic acid, the cyclic dimer thereof (lactide) or lactate esters. In particular, it relates to a separation process which includes the step of stereo selectively alcoholising a mixture of R,R- and S,S-lactide with an enzyme in the presence of a ketone solvent to produce single enantiomers of different lactic acid derivatives.

Lactic acid (2-hydroxypropanoic acid) and its cyclic dimer lactide (3,6-dimethyl-1,4-dioxan-2,5-dione) are becoming increasingly important as building blocks for the chemical and pharmaceutical industries. An example of this is in the use of lactide to manufacture polylactic acid; a polymer whose ability to be produced from a variety of renewable feedstocks and biodegradability makes it an attractive candidate to replace more conventional petrochemical polymers, such as polyethylene terephthalate, for example in the fabrication of food and beverage containers. Today, lactide is made from lactic acid which in turn is typically made by the bacterial fermentation of monosaccharides derived from crops such as maize and other natural products. Lactic acid is chiral and can be made in two enantiomeric forms (respectively L-lactic acid (also referred to as S-lactic acid) on the one hand and D-lactic acid (R-lactic acid) on the other). Derivatives such as lactide are also chiral; lactide in particular exists in two enantiomeric forms (S,S-lactide and R,R-lactide) and a third diastereomeric R,S form sometimes also referred to as meso-lactide. The conventional fermentation technologies referred to above principally generate L-lactic acid with little D-lactic acid being formed. Although these technologies can be modified using different, often genetically engineered, bacteria to produce D-lactic acid in a similarly selective manner, to date the modified bacteria and the associated processes are expensive and difficult to use reliably on a large industrial scale. This is evidenced in the comparatively higher price and limited availability of D-lactic acid.

Polylactic acid is typically prepared in two steps in which lactic acid is first dehydrated to produce lactide and then the lactide is polymerised under carefully controlled conditions to ensure that long polymer chains are produced in preference to shorter oligomers. Since, as explained above, the most readily available source of lactic acid is L-lactic acid, the lactide employed commercially to date has been S,S-lactide and the polymer produced poly-L-lactic acid (PLLA) (also known as poly-S-lactic acid). However the physical properties of PLLA are limited relative to conventional polymers (as are those of the corresponding poly-D-lactic acid (PDLA), also known as poly-R-lactic acid) which to date has limited its utility.

It has been found that these deficiencies can be overcome by using mixtures of PLLA and PDLA which are prepared by, for example, melt blending. It is believed that in these so-called 'stereocomplex' polymer mixtures close packing of the PLLA and PDLA chains occasioned by their differing chirality improves polymer crystallinity which leads to improvements in the properties referred to above. This permits the use of stereocomplex PLA for a much wider range of consumer durable applications, making it a viable alternative to traditional commodity polymers such as polyethylene terephthalate, polypropylene and polystyrene. This approach however requires access to large quantities of PDLA and therefore ultimately to large quantities of D-lactic acid.

In addition to the use of fermentation methods, it is known to produce lactic acid by a conventional chemical transformation. For example, the prior art teaches it can be made by treating monosaccharides derived from a wide range of biological material with aqueous strong base. Such processes however are not stereoselective and generate a racemic mixture of the two enantiomers in approximately equal amounts. They are therefore attractive as a way of making the precursors of stereocomplex polylactic acid. There is a problem however with using racemic lactic acid to make polylactic acid in that the resulting polymer is amorphous and therefore also has poor processing properties. It is therefore necessary to separate the enantiomers present in the racemic lactic acid or those in the corresponding racemic lactide so that the enantiomers of the latter can be polymerised separately and the two chiral polymers mixed only at the final formulation stage.

Separating a racemic mixture into its constituent enantiomers is in general terms a well-known endeavour and strategies adopted have included fractional crystallisation and chromatography. However neither of these methodologies is easy to operate on a large scale, especially in commodity scale polymer manufacturing where throughputs are high and operating costs need to be carefully controlled. What is needed therefore is a simple chemical engineering solution which can be easily and reproducibly operated at scale.

Jeon et al in Tetrahedron Letters 47 (2006) 6517-6520 disclose the laboratory observation that rac-lactide can be alcoholised with various alcohols in the presence of solvent and the supported lipase enzyme Novozym 435 to produce a product comprising a mixture of the corresponding R-alkyl lactate and the S,S alkyl lactyllactate. The preferred solvent in the Jeon disclosure is a mixture of hexane/THF. However, the present inventors have found that the use of hexane/THF in such reactions results in a heterogeneous slurry which presents difficulties for use on an industrial scale.

The present inventors have now found a flexible and efficient process that permits the production of aliphatic ester of lactic acid and aliphatic ester of lactyllactic acid on industrial scale in good yield. According to the present invention there is therefore provided a process for treating a mixture of R,R- and S,S-lactide comprising: contacting the mixture of R,R- and S,S-lactide with an aliphatic alcohol and an enzyme in the presence of a ketone solvent to produce a mixture comprising aliphatic ester of lactic acid corresponding to one lactide enantiomer and the aliphatic ester of lactyllactic acid corresponding to the other lactide enantiomer.

The invention provides a reproducible and scalable process for providing lactic acid derivatives. Surprisingly, the use of ketone solvents/co-solvents in the enzymatic resolution of rac-lactide has been found to result in high conversion of starting material to product with high enantiomeric excess, whilst displaying solubility properties amenable to industrial scale synthesis, in particular continuous/semi-continuous operations involving passing a solution containing R,R-lactide, S,S-lactide and alcohol through a packed bed of immobilised enzyme.

Preferably, the aliphatic ester of lactic acid has an enantiomeric excess of at least 90%, more preferably at least 95%, still more preferably at least 98%, yet more preferably at least 99%. Preferably, the aliphatic ester of lactyllactic acid has an enantiomeric excess of at least 90%, more preferably at least 95%, still more preferably at least 98%, still more preferably at least 99%.

The process of the present invention comprises contacting the mixture of R,R- and S,S-lactide with an aliphatic alcohol and an enzyme capable of catalysing the desired transformation in the presence of a ketone solvent. The mixture of R,R- and S,S-lactide may be racemic or scalemic. In one embodiment, the mixture of R,R- and S,S-lactide is racemic. In another embodiment, the mixture of R,R- and S,S-lactide is scalemic (i.e. non racemic).

The lactide used in this stage can in principle be derived from any source but one which is particularly suitable is racemic lactic acid produced by treating a monosaccharide (including glucose, fructose, xylose, and mixtures thereof) or a number of other carbohydrates (including formaldehyde, glyceraldehdye, dihydroxyacetone and glycerol) with a base in aqueous solution at elevated temperature. Especially preferred is the use of a Group IA, Group IIA or quaternary ammonium bases as described for example in GB2484674, the prior art discussed therein, and in U.S. Pat. No. 7,829,740. Typically the racemic lactic acid produced in these processes can be converted into racemic lactide by dehydration processes well-known in the art. It is preferred that the lactide is free or substantially free of the corresponding R,S diastereoisomer (meso lactide). If desired, R,S-lactide may be separated from R,R- and S,S-lactide, for example by routine methods well known in the art.

Suitably the aliphatic alcohol is a $C_1$ to $C_8$ alcohol, preferably a $C_2$ to $C_8$ alcohol, more preferably a $C_3$ to $C_8$ alcohol, most preferably a $C_3$ to $C_4$ alcohol. The aliphatic alcohol is preferably an alkyl alcohol, more preferably a $C_2$ to $C_8$ alkyl alcohol, still more preferably a $C_3$ to $C_8$ alkyl alcohol, yet more preferably a $C_3$-$C_4$ alkyl alcohol. The alcohol may for example be ethanol, n-propanol, i-propanol, n-butanol, s-butanol, i-butanol or 2-ethylhexanol. Examples of preferred alcohols include ethanol, n-propanol, i-propanol, and n-butanol. More preferably the alcohol is i-propanol, n-propanol or n-butanol. Still more preferably the alcohol is n-propanol or n-butanol. In one particularly preferred embodiment the alkyl alcohol is n-butanol. In another embodiment the aliphatic alcohol is i-propanol. In another embodiment the aliphatic alcohol is n-propanol.

Preferred ketone solvents include methyl ethyl ketone, methyl isobutyl ketone and, in particular, acetone.

The aliphatic alcohol/ketone solvent mixture may contain some water. Typically, the aliphatic alcohol/ketone solvent mixture employed contains less than 1% preferably less than 0.5% by weight water to ensure that the enzyme performs optimally. In some preferred embodiments, molecular sieves are used in the process.

The process may be conducted using excess aliphatic alcohol together with ketone solvent/co-solvent. It will be understood that the process may also be carried out using stoicheometric or even sub-stoicheometric quantities of aliphatic alcohol, and the ketone solvent may be the principal or only solvent. Typically the amount of aliphatic alcohol used is such that the molar ratio of aliphatic alcohol to lactide is in the range 1:1 to 10:1, preferably 2:1 to 5:1, more preferably 2:1 to 3:1.

The enzyme suitably comprises an esterase which is able to stereoselectively catalyse the reaction of aliphatic ester of lactyllactic acid with aliphatic alcohol to produce aliphatic ester of lactic acid. More preferably, the esterase is a lipase. Preferably the enzyme (e.g. the esterase, lipase) is one which is either chemically or physically immobilised on a porous support for example a polymer resin bead or a silica, alumina or aluminosilicate bead. One particularly preferred example is Lipase B, especially *Candida antarctica* Lipase B, a serine hydrolase with known enantiomeric selectivity towards the hydrolysis of secondary alcohol esters. In this aspect of the invention, the Lipase B is most preferably chemically or physically bound to micro or nano beads made of a polymer resin for example a functionalised styrene/divinylbenzene copolymer or a polyacrylate resin, as is the case for example in the commercially available material Novozym 435 as used in the disclosure by Jeon et al. As Jeon demonstrates, when this particular supported enzyme is used the aliphatic lactate ester enantiomer that is preferentially produced is that derived from R-lactic acid and the remaining aliphatic lactyllactate ester enantiomer is that derived from S-lactic acid. Other preferred enzymes include IMMCALB-T2-150, an immobilised lipase B from *Candida antarctica* covalently attached to dry acrylic beads, manufactured by Chiralvision; IMMCALBY-T2-150, a generic lipase B from *Candida antarctica* covalently attached to dry acrylic beads manufactured by Chiralvision; IMMCALB-T1-350, a lipase B from *Candida antarctica* absorbed on dry polypropylene beads, manufactured by Chiralvision; and cross-linked aggregate of lipase B from *Candida antarctica*, manufactured by CLEA. The enzyme may also be a recombinant *Candida antarctica* lipase B from *Aspergillus oryzae*, supplied by Sigma Aldrich (non-immobilised).

The process is suitably carried out at a temperature in the range of from 15 to 140° C. in order to ensure that reaction rates are significant on the one hand and that the enzyme does not deteriorate with long term use on the other. Preferably the temperature employed is in the range 25 to 80° C. most preferably 30 to 70° C.

Typically, when an enzyme such as a *Candida antarctica* lipase B (e.g. Novozym 435) is used, the aliphatic ester of lactic acid and the aliphatic ester of lactyllactic acid are respectively an aliphatic ester of R-lactic acid and an aliphatic ester of S,S-lactyllactic acid. By varying the reaction conditions it may be possible to alter the enzyme selectivity. Thus in another, less preferred, embodiment the enzyme is a *Candida antarctica* lipase B, and the aliphatic ester of lactic acid and the aliphatic ester of lactyllactic acid are respectively an aliphatic ester of S-lactic acid and an aliphatic ester of R,R-lactyllactic acid. The process can be carried out on an industrial scale in a number of ways. For example, if a supported enzyme is used the reaction can be carried out batchwise in a single stirred or highly back-mixed tank after which the supported enzyme is separated, e.g. by filtration or the use of hydrocyclones, and the purified liquid may be fed to the kettle of a distillation column. In such a case the residence time of the reactants and the enzyme in the stirred tank will typically be in the range up to 24 preferably up to 10, more preferably from 1 to 8 hours, and the amount of supported enzyme used will be in the range up to 10% preferably up to 5% by weight of the racemic lactide used.

Use of the ketone solvent/co-solvent facilitates continuous or semi-continuous flow operations. Thus, in a preferred embodiment, the process may be operated as a continuous or semi-continuous process. For example, a mixture containing e.g. R,R-lactide and S,S-lactide, alkyl alcohol (e.g. n-butanol) and ketone solvent (e.g. acetone) may be brought into contact with the enzyme (e.g. an immobilised enzyme such as Novozym-435) by passing the mixture through a packed bed of enzyme (e.g. present in a column). In such flow processes, the residency time is selected so as to ensure high conversion. In a particularly preferred embodiment, the packed bed is vertical, and the mixture is fed into the top of the column. In one preferred embodiment, the process is carried out continuously in a tower reactor by for example trickling the liquid reactants down though a fixed or fluidised bed of the supported enzyme contained therein. A product mixture comprising aliphatic ester of lactic acid, aliphatic ester of lactyllactic acid and optionally unreacted lactide, unreacted alcohol and ketone solvent can then be recovered from the bottom of the tower. In this arrangement, the contact time of the reactants with the bed is typically in the range of up to 24 hours. Preferably residency times (contact time of the reactants with the bed) are in the range of from 10 minutes to 4 hours, more preferably from 10 minutes to 2 hours.

Where the process is operated in a batch-type reactor, the enzyme may for example be separated from the mixture containing aliphatic ester of lactic acid and aliphatic ester of lactyllactic acid by filtration of the enzyme, or by decanting or siphoning off liquid mixture prior to distillation. Preferably, in the case of a batch-type process, the enzyme is re-used at least once, more preferably at least twice, still more preferably at least 5 times, yet more preferably at least 10 times, most preferably at least 20 times.

In the case of a continuous process where R,R-lactide, S,S-lactide and alcohol are passed through a packed bed of enzyme (i.e. a continuous or semi-continuous flow process), product and enzyme are continually being separated from one another and the enzyme is continually being recycled. Accordingly, in one preferred embodiment, the process of the invention is a continuous or semi-continuous process which comprises contacting the mixture of R,R- and S,S-lactide with an aliphatic alcohol (e.g. n-butanol) and an enzyme (e.g. Novozym 435) in the presence of a ketone solvent (e.g. acetone) to produce a mixture comprising aliphatic ester of lactic acid corresponding to one lactide enantiomer and the aliphatic ester of lactyllactic acid corresponding to the other lactide enantiomer, by passing a solution containing R,R- and S,S-lactide, aliphatic alcohol and ketone co-solvent through a packed bed of immobilised enzyme.

Preferably aliphatic ester of lactic acid and/or aliphatic ester of lactyllactic acid are recovered by distillation, more preferably by distillation under reduced pressure. For example, aliphatic ester of lactic acid (e.g. n-butyl lactate, i-propyl lactate, n-propyl lactate) may be separated from aliphatic ester of lactyllactic acid (e.g. n-butyl lactyllactate, i-propyl lactyllactate, n-propyl lactyllactate) by fractional distillation at a pressure of from 100 Pa (1 mbar) to 10,000 Pa (100 mbar), preferably 1,000 Pa (10 mbar) to 5,000 Pa (50 mbar), more preferably at a pressure of from 2,000 Pa (20 mbar) to 4,000 Pa (40 mbar), and at a temperature of from 40° C. to 170° C., preferably 50° C. to 120° C., more preferably at a temperature of from 75° C. to 110° C.

In that case, at least the lower boiling aliphatic lactate ester fraction is removed overhead for further use or treatment, thereby indirectly effecting separation of the two lactic acid enantiomers. In a preferred embodiment, the aliphatic ester of lactic acid is removed overhead by distillation, and the distillation residue comprises the aliphatic ester of lactyllactic acid, which may be removed via a side stream. In an alternative embodiment, both the aliphatic ester of lactic acid and the aliphatic ester of lactyllactic acid are removed overhead by distillation (e.g. they are collected as separate overhead product streams, for example at different temperatures and/or pressures).

The distillation column (also known as a fractionating column) used must have the necessary number of theoretical plates to perform its function (i.e. to enable separation of aliphatic ester of lactic acid form aliphatic ester of lactyllactic acid). In the case where the reaction is carried out batchwise the reaction will likely have gone to completion and the residuum in the boiler of the distillation column will generally comprise an aliphatic lactyllactate ester fraction which can then be removed by a side stream for its own further treatment and use. If the process of the invention is operated continuously then the distillation column will also operate continuously with recycle to ensure that at steady state the aliphatic ester of R- or S-lactic acid and/or the aliphatic ester of R,R- or S,S-lactyllactic acid can be recovered quantitatively and in optically pure form. In this continuously operated case the distillation can be effected in either a single column or a train of columns arranged in series. Typically the distillation column(s) used in step (c) are operated at a pressure of less than 5000 Pa.

Ketones such as acetone have boiling points such that they can readily be separated from aliphatic ester of lactic acid and aliphatic ester of lactyllactic acid by distillation, allowing recycling of the solvent.

In an embodiment of the present invention the single enantiomer of the aliphatic lactate ester can be converted to either the corresponding lactic acid enantiomer or to the corresponding lactide enantiomer. In both cases, the aliphatic alcohol is released and can be separated and recycled. For example, in the case where the supported enzyme used is Novozym 435, the aliphatic alcohol is n-butanol and the solvent/co-solvent is acetone, the R-n-butyl lactate so generated can be converted to R-lactic acid or R,R-lactide. If R,R-lactide is produced it can then be polymerised to produce optically pure PDLA. Likewise, the single enantiomer of the aliphatic lactyllactate ester can be converted back to either the corresponding lactic acid or lactide enantiomer so that for example in the case that the aliphatic ester of lactyllactic acid is S,S-n-butyl lactyllactate, it can be hydrolysed to S-lactic acid or converted into S,S-lactide, which can then be polymerised to produce optically pure PLLA.

Thus, according to a first further embodiment of the present invention there is provided a process for producing S-lactic acid characterised by the steps of: contacting a mixture of R,R- and S,S-lactide with an aliphatic alcohol (e.g. a $C_1$ to $C_8$ alkyl alcohol) and an enzyme in the presence of a ketone solvent to produce a mixture comprising aliphatic ester of lactic acid corresponding to one lactide enantiomer, and aliphatic ester of lactyllactic acid corresponding to the other lactide enantiomer; separating the aliphatic ester of lactic acid from the aliphatic ester of lactyllactic acid by fractional distillation; and either, where the aliphatic ester of lactyllactic acid is an aliphatic ester of S,S-lactyllactic acid, hydrolysing the aliphatic ester of S,S-lactyllactic acid to produce S-lactic acid or, where the aliphatic ester of lactic acid is an aliphatic ester of S-lactic acid, hydrolysing the aliphatic ester of S-lactic acid to produce S-lactic acid. Preferably, the mixture of R,R- and S,S-lactide used in the process has been prepared from a mixture of R- and S-lactic acid. The S-lactic acid produced by the process preferably has an enantiomeric excess of at least 90%, more preferably at least 95%, still more preferably at least 98%, most preferably at least 99%.

Alternatively, according to a second further embodiment of the present invention there is provided a process for producing R,R-lactide characterised by the steps of contacting a mixture of R,R- and S,S-lactide with an aliphatic alcohol (e.g. a $C_1$ to $C_8$ alkyl alcohol) and an enzyme in the presence of a ketone solvent to produce a mixture comprising aliphatic ester of lactic acid corresponding to one lactide enantiomer, and aliphatic ester of lactyllactic acid corresponding to the other lactide enantiomer; separating the aliphatic ester of lactic acid from the aliphatic ester of lactyllactic acid by fractional distillation; and either, where the aliphatic ester of lactyllactic acid is an aliphatic ester of R,R-lactyllactic acid, converting the aliphatic ester of R,R-lactyllactic acid to R,R-lactide or, where the aliphatic ester of lactic acid is an aliphatic ester of R-lactic acid, converting the aliphatic ester of R-lactic acid to R,R-lactide. Preferably, the mixture of R,R- and S,S-lactide used in the process has been prepared from a mixture of R- and S-lactic acid. The R,R-lactide produced by the process preferably has an enantiomeric excess of at least 90%, more preferably at least 95%, still more preferably at least 98%, most preferably at least 99%.

Alternatively in a third further embodiment of the present invention there is provided a process for producing R-lactic acid characterised by the steps of: contacting a mixture of R,R- and S,S-lactide with an aliphatic alcohol (e.g. a $C_1$ to $C_8$ alkyl alcohol) and an enzyme in the presence of a ketone solvent to produce a mixture comprising aliphatic ester of lactic acid corresponding to one lactide enantiomer, and aliphatic ester of lactyllactic acid corresponding to the other lactide enantiomer; separating the aliphatic ester of lactic acid from the aliphatic ester of lactyllactic acid by fractional distillation; and either, where the aliphatic ester of lactyllactic acid is an aliphatic ester of R,R-lactyllactic acid, hydrolysing the aliphatic ester of R,R-lactyllactic acid to produce R-lactic acid or, where the aliphatic ester of lactic acid is an aliphatic ester of R-lactic acid, hydrolysing the aliphatic ester of R-lactic acid to produce R-lactic acid. Preferably, the mixture of R,R- and S,S-lactide used in the process has been produced from a mixture of R- and S-lactic acid. The R-lactic acid produced by the process preferably has an enantiomeric excess of at least 90%, more preferably at least 95%, still more preferably at least 98%, most preferably at least 99%.

Alternatively, in a fourth further embodiment there is provided a process for producing S,S-lactide characterised by the steps of contacting a mixture of R,R- and S,S-lactide with an aliphatic alcohol (e.g. a $C_1$ to $C_8$ alkyl alcohol) and an enzyme in the presence of a ketone solvent to produce a mixture comprising aliphatic ester of lactic acid corresponding to one lactide enantiomer, and aliphatic ester of lactyllactic acid corresponding to the other lactide enantiomer; separating the aliphatic ester of lactic acid from the aliphatic ester of lactyllactic acid by fractional distillation; and either, where the aliphatic ester of lactyllactic acid is an aliphatic ester of S,S-lactyllactic acid, converting the aliphatic ester of S,S-lactyllactic acid to S,S-lactide or, where the aliphatic ester of lactic acid is an aliphatic ester of S-lactic acid, converting the aliphatic ester of S-lactic acid to S,S-lactide. Preferably, the mixture of R,R- and S,S-lactide used in the process has been prepared from R- and S-lactic acid. The S,S-lactide produced by the process preferably has an enantiomeric excess of at least 90%, more preferably at least 95%, still more preferably at least 98%, most preferably at least 99%.

Conversion of the mixture of R- and S-lactic acid into a mixture of R,R and S,S-lactide may result in formation of R,S-lactide, as well as R,R- and S,S-lactide. If desired, R,S-lactide may be separated from R,R- and S,S-lactide by routine methods well known in the art.

Preferably the R,R- and S,S-lactides produced in respectively the second or fourth further embodiments set out above are separately polymerised to produce substantially optically pure PDLA or PLLA. PDLA and PLLA can be combined in varying proportions, for example using melt blending, to produce a range of stereocomplex polylactic acid formulations having an associated range of improved optical and form stability properties relative to either PLLA or PDLA alone. Whilst the relative proportions of these two polymers can vary widely it is preferred that the PLLA content of these formulations lie in the range 40 to 60% based on the total weight of PLLA and PDLA. The stereocomplex polymers so produced can be used in a wide range of applications, including a wider scope of durable uses previously not possible with PLLA.

The invention will now be illustrated by reference to the following examples.

EXAMPLE 1

Stereoselective Alcoholysis of Rac-Lactide in Butanol/Acetone Mixture (Batch)

A glass vessel was charged with rac-lactide (2.30 g), Novozym 435 (115 mg, 5 wt % with respect to lactide), n-butanol (2.9 ml, 2:1 molar ratio with respect to lactide) then acetone (6.8 ml). The mixture was shaken by hand at RT to 45° C. to ensure that the lactide dissolves. The vessel was then placed in a heated shaker (45° C., 750 rpm (t=0). The reaction was monitored over 24 hrs. Samples were analysed by chiral gas chromatography to determine the (S)-butyl lactate, (R)-butyl lactate, (S,S)-butyl lactyllactate, (R,R)-butyl lactyllactate, (S,S)-lactide and (R,R)-lactide composition. After 24 hrs the reaction reached 89% conversion to (S)-butyl lactate (based on theoretical yield) at an optical purity >99% e.e.

EXAMPLES 2-4

Stereoselective Alcoholysis of Rac-Lactide in Butanol/Co-Solvent Mixtures and Recycle of Enzyme (Batch)

Rac-lactide (1.45 g, 10 mmol) was alcoholised with n-BuOH (2.75 ml, 30 mmol, 3 eq.) and Novozym 435 (200 mg, 14%) for 7 h at 35° C. in the presence of 2.75 ml of the following co-solvents: acetone, tert-BuOH, control (n-BuOH as only solvent). After 7 h each reaction was stopped and analysed for conversion to R-butyl lactate. The reaction liquors were then carefully separated from the immobilised enzyme by syringe and the enzyme was washed with the respective solvent and reused in a subsequent run. The enzyme was reused for up to 8 runs in total.

Conversion to R-butyl lactate after the $1^{st}$ and $8^{th}$ runs was:

| Example | Solvent | Run 1 conversion (%) | Run 8 conversion (%) |
|---|---|---|---|
| 2 | Acetone | 92 | 79 |
| 3 | tBuOH* | 92 | 35 |
| 4 | n-BuOH* (control) | 94 | 38 |

*Comparative example

EXAMPLE 5

Stereoselective Alcoholysis of Rac-Lactide in Butanol/Acetone Mixture with Recycle of Enzyme (Continuous)

At regular intervals a 50:50 mixture of (S,S)- and (R,R)-lactide was dissolved in acetone at a concentration of 30% wt lactide in a 1 liter water heated jacketed vessel at 45° C. equipped with a reflux condenser. n-Butanol was then added to the lactide solution so that the n-BuOH/lactide molar ratio was 2:1: at 45° C. under these conditions the lactide remains in solution. Typical batches were prepared to supply the reaction rig with sufficient substrate to operate for at least 24 h.

The contents were then fed through a 400 mm length reflux column, the exterior collar of which was heated to 45° C.

using recirculated heated water. The column was fitted directly onto a glass adaptor containing a 5 g packed bed of Novozym 435 (supported *Candida antarctica* Lipase B). The solution was fed through the column using a Watson Marlow 120S peristaltic pump and 1.6 mm ID Marprene tubing. Once passed through the enzyme bed the product mixture was collected and samples analysed by gas chromatography. Flow of reactants over the enzyme bed was adjusted to achieve a conversion of (R,R)-butyl lactyllactate into R-butyl lactate in the region 80-90%. Even after three months continuous operation conversions were >80% and the optical purity of the R-butyl lactate >99% e.e.

EXAMPLE 6

Stereoselective Alcoholysis of Rac-Lactide in Butanol/Methyl Ethyl Ketone (MEK) Mixture with Recycle (Continuous)

A solution of 10 g rac-lactide, 15 g BuOH, (3 Eq), and 50 g MEK (a ratio of 1:1.5:5) was passed through a steel column containing 0.500 g Novozym 435 immobilised *Candidia antarctica* Lipase B over a period of 60 h. Samples for analysis were taken at 2 hourly intervals from the feed and from the output of the column and the concentrations of (S)-butyl lactate, (R)-butyl lactate, (S,S)-butyl lactyllactate, (R,R)-butyl lactyllactate, (S,S)-lactide and (R,R)-lactide were determined by chiral liquid chromatography (no S-butyl lactate was detected). The conversion remained steady at 85% and the R-butyl lactate products were all >99% enantiomeric excess.

EXAMPLE 7

Distillation of Acetone and Butanol from Butyl Lactate and Butyl Lactyllactate

A 1 liter 3-necked glass flask was fitted with a magnetic stirrer bar and an insulated 20-plate Oldershaw column surmounted by a Perkin vacuum still head with 250 ml receiver. A feed point approximately half-way up the column allowed feedstock to be charged via a peristaltic pump using PharMed® BPT peristaltic tubing. The flask was heated using an oil bath and vacuum was applied via a Teflon diaphragm pump, with a solid $CO_2$ cooled trap.

The feedstock for this distillation consisted of acetone (49% wt); (R)-n-butyl lactate (21% wt); butanol (7% wt); (R,R)-n-butyl lactyllactate (3% wt) and (S,S)-n-butyl lactyllactate (19% wt). The remaining components included trace quantities of (S)-n-butyl lactate and both (S,S)- and (R,R)-lactides.

Initially, some extra butanol was added to the feed charged in order to establish continuous distillation conditions, since the amount of butanol present in the feedstock was low. Once this had been established (oil bath ~135° C., internal temp. ~117° C., still head temp. ~77° C., vacuum=500 mBarA), the main feed was then charged at 2.5-5.0 ml/min. Fractions were collected as detailed below and analysed by chiral GC.

From the 702 ml (609.5 g) of feedstock used, the composition of the resulting concentrated product (340.11 g) was: acetone (4.5%); (R)-n-butyl lactate (44.3%); n-butanol (4.7%); (R,R)-n-butyl lactyllactate (5.9%), (S,S)-n-butyl lactyllactate (39.0%) and (S)-n-butyl lactate (0.7%) with the remainder being (S,S)- and (R,R)-lactides.

The composition of the volatile products collected in the cold trap (59.7 g) was: acetone (89%) and butanol (10%) with the remaining 1% being n-butyl lactate.

A continuous distillation set up was constructed comprising a 250 ml Hastelloy reboiler (with sightglass), a trace-heated 20-plate Oldershaw column surmounted by a Perkin vacuum still head with 250 ml receiver. There was a feed point approximately half-way up the column allowing feedstock to be charged via a peristaltic pump using PharMed® BPT peristaltic tubing. The temperature of the reboiler and column heat tracing were electrically controlled. Vacuum was applied via a Teflon diaphragm pump, with a solid $CO_2$ cooled trap.

The feedstock for this distillation (1050.0 g) consisted of: acetone (49% wt); (R)-n-butyl lactate (21% wt); butanol (7% wt); (R,R)-n-butyl lactyllactate (3% wt) and (S,S)-n-butyl lactyllactate (19% wt) with traces of (S)-n-butyl lactate and both (S,S)- and (R,R)-lactides.

After the initial filling and conditioning of the column, the feedstock was fed in and rates and temperatures adjusted until steady continuous distillation was achieved. The optimum conditions were found to be vacuum=100 mBarA; reboiler temperature=100° C.; Heat tracing=65° C.; Feed rate=4 ml/min.

These conditions were maintained throughout this distillation, and resulted in the product distribution detailed below. This procedure successfully concentrated the higher-boiling components (mainly (R)-n-butyl lactate and (S,S)-n-butyl lactyllactate) in the reboiler in high yields. Acetone and butanol recovery is also high and these solvents may be recycled to earlier stages of the overall process.

| Fraction | Oil bath temp./° C. | Internal temp./° C. | Head temp. (° C.) | Vacuum (mBarA) | Mass of fraction (g) | Composition by GC (%) | | |
|---|---|---|---|---|---|---|---|---|
| | | | | | | Acetone | Butanol | (R)-Butyl lactate |
| A | 135-149 | 117-135 | 70-76 | 500 | 45.3 | 99.5 | 0.0 | 0.5 |
| B | 148-154 | 136-148 | 36-66 | 500 | 25.1 | 98.6 | 0.9 | 0.5 |
| C | 147-153 | 138-147 | 30-36 | 500 | 10.1 | 96.1 | 3.4 | 0.5 |

| Details | Amount (g) | Composition by GC (%) | | | | | | |
|---|---|---|---|---|---|---|---|---|
| | | Acetone | Butanol | (S)-BuLa | (R)-BuLa | (S,S)-BuLaLa | (R,R)-BuLaLa | (S,S)-Lactide | (R,R)-Lactide |
| Feed-Stock | 1050.0 | 48.1 | 7.8 | 0.1 | 21.6 | 19.4 | 2.7 | 0.1 | 0.2 |
| Distillates | 63.4 | 11.0 | 53.6 | 0.2 | 28.9 | 5.6 | 0.8 | 0.0 | 0.0 |
| Reboiler Fractions | 335.3 | 0.4 | 3.5 | 0.2 | 45.0 | 44.3 | 6.3 | 0.1 | 0.3 |
| Cold Trap | 422.2 | 95.3 | 4.3 | 0.2 | 0.2 | 0.1 | 0.0 | 0.0 | 0.0 |
| Sampling | 126.8 | 4.6 | 10.3 | 0.7 | 24.9 | 24.4 | 3.5 | 0.0 | 0.2 |

BuLa = butyl lactate; BuLaLa = butyl lactyl lactate

EXAMPLE 8

Distillation of Butyl Lactate from Butyl Lactyllactate

A continuous distillation apparatus was constructed comprising a 250 ml Hastelloy reboiler with sightglass fitted with a heated 20-plate Oldershaw column surmounted by a Perkin vacuum still head with 250 ml receiver. There was a feed point approximately half-way up the column allowing feedstock to be charged via a peristaltic pump using PharMed® BPT peristaltic tubing. The temperature of the reboiler and column heat tracing were electrically controlled. Vacuum was applied via a Teflon diaphragm pump, with a solid $CO_2$ cooled trap.

The feedstock for this distillation (740.5 g) consisted of: acetone (<0.5%); (R)-n-butyl lactate (46%); butanol (3%); (R,R)-n-butyl lactyllactate (6%) and (S,S)-n-butyl lactyllactate (44%) with trace quantities (<0.5%) of (S)-n-butyl lactate and both (S,S)- and (R,R)-lactides.

After the initial filling and conditioning of the column, the feedstock was fed in and rates and temperatures adjusted until steady continuous distillation was achieved. The optimum conditions were found to be: Vacuum=35 mBarA; reboiler temperature=150° C.; Heat tracing=110° C.; Feed rate=1-4 ml/min. These conditions were maintained throughout this distillation, and resulted in the product distribution detailed below:

| Details | Mass (g) | Composition by GC (%) | | | | | | |
|---|---|---|---|---|---|---|---|---|
| | | Acetone | BuOH | (S)-BuLa | (R)-BuLa | (S,S)-BuLaLa | (R,R)-BuLaLa | (S,S)-Lactide | (R,R)-Lactide |
| Feed | 740.5 | 0.2 | 3.2 | 0.2 | 45.9 | 44.0 | 6.3 | 0.1 | 0.2 |
| Distillate | 277.6 | 0.0 | 5.0 | 0.4 | 93.9 | 0.5 | 0.1 | 0.0 | 0.1 |
| Reboiler Fractions | 389.6 | 0.0 | 0.3 | 0.2 | 17.7 | 70.7 | 10.3 | 0.3 | 0.5 |
| Cold Trap | 10.6 | 12.0 | 76.1 | 0.9 | 10.8 | 0.1 | 0.0 | 0.0 | 0.0 |
| Sampling | 53.1 | 2.6 | 0.7 | 0.2 | 16.1 | 69.5 | 10.3 | 0.2 | 0.4 |

BuLa = butyl lactate; BuLaLa = butyl lactyl lactate

The distilled product analysed as 93.9% (R)-butyl lactate; 0.4% (S)-butyl lactate, 5.0% butanol; 0.5% (S,S)-butyl lactyllactate; 0.1% (R,R)-butyl lactyllactate and 0.1% (R,R)-lactide.

EXAMPLE 9

Solubility of Lactide

The solubility of lactide in different solvents was investigated. Solubility was ranked in the following order: Acetone>>n-BuOH>t-BuOH.

The solubility of lactide in a n-BuOH/acetone system at 35° C. with 3 equivalents of alcohol was found to be as follows: 1.44 g lactide (10 mmol)/2.23 g n-BuOH (2.75 ml)/3.17 g $Me_2CO$ (4 ml) (i.e. 1:1.45 v/v or 1:1.42 w/w n-BuOH:acetone).

The invention claimed is:

1. A process for producing an aliphatic ester of lactic acid and an aliphatic ester of lactyllactic acid, one of said esters being in the R form and the other being in the S form, comprising:
contacting a mixture of R,R- and S,S-lactide with an aliphatic alcohol and an enzyme in the presence of a ketone solvent
and producing a mixture comprising the aliphatic ester of lactic acid corresponding to one lactide enantiomer (R or S) and the aliphatic ester of lactyllactic acid corresponding to the other lactide enantiomer (S or R).

2. A process as claimed in claim 1, wherein the ketone solvent is selected from the group consisting of acetone, methyl ethyl ketone and methyl isobutyl ketone.

3. The process as claimed in claim 1, wherein the aliphatic ester of lactic acid has an enantiomeric excess of at least 90%.

4. The process as claimed in claim 1, wherein aliphatic ester of lactyllactic acid has an enantiomeric excess of at least 90%.

5. The process as claimed in claim 1, wherein the aliphatic alcohol is a $C_2$ to $C_8$ aliphatic alcohol.

6. The process as claimed in claim 5, wherein the molar ratio of $C_2$ to $C_8$ aliphatic alcohol to racemic lactide is in the range 2:1 to 5:1.

7. The process as claimed in claim 5, wherein the $C_2$ to $C_8$ aliphatic alcohol (a) is n-butanol.

8. The process as claimed in claim 1, wherein the enzyme is a *Candida antarctica* lipase B, and the aliphatic ester of lactic acid and the aliphatic ester of lactyllactic acid are respectively an aliphatic ester of R-lactic acid and an aliphatic ester of S,S-lactyllactic acid.

9. The process as claimed in claim 1, wherein the enzyme is chemically or physically immobilised on a porous support.

10. The process as claimed in claim 1, which comprises the further step of converting one or both of the aliphatic ester of lactyllactic acid and the aliphatic ester of lactic acid into the corresponding R,R- or S,S-enantiomer of lactide and/or the corresponding R- or S-enantiomer of lactic acid.

11. The process as claimed in claim 1, wherein the mixture of R,R- and S,S-lactide has been prepared from a mixture of R- and S-lactic acid.

12. The process as claimed in claim 11, wherein the mixture of R- and S-lactic acid has been prepared by treating a monosaccharide or glycerol with a base.

13. The process according to claim 1, wherein the process comprises separating the aliphatic ester of lactic acid from the aliphatic ester of lactyllactic acid by fractional distillation; and either, where the aliphatic ester of lactyllactic acid is an aliphatic ester of S,S-lactyllactic acid, the process comprises hydrolysing the aliphatic ester of S,S-lactyllactic acid to produce S-lactic acid or, where the aliphatic ester of lactic acid is an aliphatic ester of S-lactic acid, the process comprises hydrolysing the aliphatic ester of S-lactic acid to produce S-lactic acid.

14. The process according to claim 1, wherein the process comprises separating the aliphatic ester of lactic acid from the aliphatic ester of lactyllactic acid by fractional distillation; and either, where the aliphatic ester of lactyllactic acid is an aliphatic ester of R,R-lactyllactic acid, the process comprises hydrolysing the aliphatic ester of R,R-lactyllactic acid to produce R-lactic acid or, where the aliphatic ester of lactic acid is an aliphatic ester of R-lactic acid, the process comprises hydrolysing the aliphatic ester of R-lactic acid to produce R-lactic acid.

15. The process according to claim 1, wherein the process comprises separating the aliphatic ester of lactic acid from the aliphatic ester of lactyllactic acid by fractional distillation; and either, where the aliphatic ester of lactyllactic acid is an aliphatic ester of R,R-lactyllactic acid, the process comprises converting the aliphatic ester of R,R-lactyllactic acid to R,R-lactide or, where the aliphatic ester of lactic acid is an aliphatic ester of R-lactic acid, the process comprises converting the aliphatic ester of R-lactic acid to R,R-lactide.

16. The process as claimed in claim 15, wherein the R,R-lactide produced is polymerised to produce poly-R-lactic acid.

17. The process as claimed in claim 16, wherein the poly-R-lactic acid produced is melt blended to form stereocomplex polylactic acid.

18. The process according to claim 1 wherein the process comprises separating the aliphatic ester of lactic acid from the aliphatic ester of lactyllactic acid by fractional distillation; and either, where the aliphatic ester of lactyllactic acid is an aliphatic ester of S,S-lactyllactic acid, the process comprises converting the aliphatic ester of S,S-lactyllactic acid to S,S-lactide or, where the aliphatic ester of lactic acid is an aliphatic ester of S-lactic acid, the process comprises converting the aliphatic ester of S-lactic acid to S,S-lactide.

19. The process as claimed in claim 18, wherein the S,S-lactide produced is polymerized to produce poly-S-lactic acid.

20. The process as claimed in claim 19, wherein the poly-S-lactic acid produced is melt blended to form stereocomplex polylactic acid.

* * * * *